United States Patent [19]

Alfonsi

[11] Patent Number: 4,520,012

[45] Date of Patent: May 28, 1985

[54] COMPOSITION OF MATTER FOR IMPROVING HAIR GROWTH

[76] Inventor: Marguerite Alfonsi, Batiment F-1-Allée des Glaieuls, 91130 Ris Orangis, France

[21] Appl. No.: 345,446

[22] Filed: Feb. 3, 1982

[30] Foreign Application Priority Data

Feb. 3, 1981 [FR] France ................... 81 02010

[51] Int. Cl.³ .................. A61K 35/12; A61K 35/78
[52] U.S. Cl. ................................ 424/95; 424/195.1
[58] Field of Search ............................ 424/95, 195

[56] References Cited

FOREIGN PATENT DOCUMENTS 2070045  9/1981  France .

OTHER PUBLICATIONS

Derwent Abstract 77488s 12/31/1969.

*Primary Examiner*—Stanley J. Friedman
*Assistant Examiner*—John W. Rollins
*Attorney, Agent, or Firm*—Sughrue, Mion, Zinn, Macpeak & Seas

[57] ABSTRACT

The scalp is first cleaned with a lotion comprising one half of mineral oil and one half of 70° alcohol, in which lotion plants have macerated. After that is applied a cream containing principally marrow and additions of bergamot oil, alcohol, oil and sulphur.

12 Claims, No Drawings

COMPOSITION OF MATTER FOR IMPROVING HAIR GROWTH

The present invention relates to means for treating the scalp and more particularly to compositions of matter for a treatment insuring to the hair system a normal development, especially in the cases where it is falling, for example as a consequence of an illness, a pregnancy or after an agressive treatment such as a permanent wave hairdressing. The composition of matter according to the invention is more particularly suited for women's hair. Nevertheless, it may be helpful in certain cases for men's hair.

The present invention has more particularly for its object a composition of matter in which the combination of ingredients presents surprising synergic properties, that the mere addition of their particular properties do not allow to foresee.

After a preferable special preparation of the skin, the application of a cream according to the present invention provides with the necessary nutritive elements and also stimulates the biological processes of development or redevelopment of the hair system.

Many treatments against hair loss have already been proposed but so far it does not appear that a true revival of the hair system by simple and cheap means has really been achieved. The means according to the invention need neither complicated apparatus or processes nor specialized staff.

In prior French Pat. No. 2,070,045 of Applicant filed Dec. 31, 1969, is disclosed a three-phase treatment including first a cleaning with oil, then a treatment with a composition comprising mineral oil and finally a treatment with a nourishing cream.

According to present invention, improved results are obtained by using a more simple technique and more especially by the application of a composition of matter formed of a cream containing basically marrow, which action develops at the level of keratin and roots of the hair, stopping the hair loss, stimulating the nourishment, especially during growth and regeneration.

According to present invention, there is made on the scalp an application of a cream comprising the following ingredients with a percentage given in weight:

bergamot oil: 0.75 to 2
Vegetable alcohol: 1 to 4
Marrow: at least 90
Oil: 2 to 5
Flowers of sulphur: 1 to 3

Preferably, the scalp is previously washed with a lotion comprising substantially the same amount of non deodorized mineral oil and 70° alcohol, in which have soaked during about one month the following plants: rosemary, thyme, clove, sage, lavender and flowers and seeds of nasturtium and camomile.

Various other objects, features and attendant advantages of the present invention will be more fully appreciated as the same becomes better understood from the following detailed description of the present invention.

Reference will be made to the scalp, as an illustration, but experience has proven that the means of the invention may be useful for other areas of the skin.

A cream is prepared by mixing at about 40° C., in the preferred following proportions, given in weight:
Bergamot oil: 1
Vegetable alcohol: 2
Marrow: 92
Oil: 4
Flowers of sulphur: 1

Checkings for trying to modify the above proportions have allowed to determine the following limits for the various ingredients.

Bergamot oil: the proportion should be comprised between 0.75 and 2%. An amount of 0.5% has proven unsufficient. With 2%, the results are good but the product is somewhat agressive. If the amount is substantially above 2%, say for example 5%, the bergamot oil may cause hair loss so that the result is opposed to that which is aimed at.

Vegetable alcohol: the activity is due to the plant spirits which are found for example in rum. It is not the alcohol itself which is active although it has a cleaning and a germ-killing effect. An amount of 3 to 4% may be used. With a greater amount, the composition may become aggressive although alcohol alone diluted to that degree cannot injure the skin.

Marrow. Beef marrow is used since it is cheap and easy to provide. At least 90% is necessary. The amount may be greater without drawback, but that would reduce the amount of the other ingredients what would weaken the efficiency of the composition.

Oil. A slight amount has proven of advantage. 2 to 5% should be used. Either petroleum jelly or a vegetable oil such as sesame, olive, almond or the like may be used. In a preferred embodiment there is used one half petroleum jelly, one half vegetable oil. A greater amount is not necessary nor harmful, but that would reduce the amount of marrow, and the efficiency of the composition would sink down.

Sulphur helps the formation of keratin. With an amount less than 1%, the efficiency of the composition substantially sinks down. It is possible to introduce more than 1%. For example 2 to 3%. With an amount increasing above 3% there is no more improvement of the composition, and the latter becomes noxious.

For applying the composition of the present invention, the scalp is carefully cleaned with a cotton pad or the like impregnated with a lotion comprising substantially the same amount of non-deodorized mineral oil and 70% ethyl alcohol in which have soaked during about one month the following plants: rosemary, thyme, clove, sage, lavender and flowers and seeds of nasturtium and camomile. This balance of amounts between mineral oil and alcohol has proven satisfactory. It is well understood that a proportion slightly different from this preferable proportion remains within the scope of the present invention. After about 15 to 20 minutes, the cream above defined is applied while massaging along two perpendicular directions for five minutes, to help the cream penetrate into the skin. The cream is maintained during at least 20 minutes and preferably several hours if possible (overnight for example) after what the scalp is washed.

With this treatment, applied once a week during one month, every other week the following month and once the third month, the hair grows in most cases, that is after 3 to 8 weeks of treatment.

Most of the time this three-month treatment is sufficient.

The experience has permitted to establish that the association of bergamot oil with marrow and other lipids not only stimulate hair growth but also enhance blood circulation in the derm and nourishes hair. It is possible that the effect is due, amongst others, to the action of the psoralenes of bergamot, and particularly the 5-methoxy-psoralene.

Four cases will be described in the purpose of illustrating the present invention. The following results have been noted.

(1) A 7-year old child with very thin hair obtains active and strong growth of 1.5 cm every month after a treatment such as described hereabove.

(2) A 32-year old woman with sick and broken hair which tend to fall obtained after 7 weeks of treatment a strong hair with normal appearance.

(3) 72-year old women with scarce hair. After two months of the above treatment a normal hair growth resulted.

(4) 45-year old man with eczema on the scalp. The above treatment has produced a quick desquamation (peeling), a regeneration of derm and keratin, and a normal growth after nine weeks.

The applicant has received many letters from people who have been satisfied after using the composition of present invention in the curing of hair and scalp. In all cases the skin of the scalp has been improved. Further the above defined composition provides also noticeable fungicide and germ-killing properties, what is a substantial advantage.

I claim:

1. A complex for treating the scalp, comprising at least the second of the following two products:
(A) a lotion for preliminary use comprising substantially the same amount of non deodorized mineral oil and 70% ethyl alcohol, in which have soaked during about one month the following plants: rosemary, thyme, clove, sage, lavender and flowers and seeds of nasturtium and camomile;
(B) a cream comprising the following ingredients with a percentage given in weight:
Bergamot oil: 0.75 to 2
Vegetable alcohol: 1 to 4
Marrow: at least 90
Oil: 2 to 5
Flowers of sulphur: 1 to 3.

2. The complex according to claim 1 wherein the percentages of the cream under B are substantially the following:
Bergamot oil: 1
Vegetable alcohol: 2
Marrow: 92
Oil: 4
Flowers of sulphur: 1.

3. The complex according to claims 1 or 2 wherein the vegetable alcohol is rum.

4. The complex according to claims 1 or 2, wherein the oil comprises one half petroleum jelly and one half vegetable oil.

5. The complex according to claim 3 wherein the oil comprises one half petroleum jelly and one half vegetable oil.

6. The complex according to claims 1, 2 or 5, wherein the oil is selected from the group consisting of oils of sesame, olive and almond.

7. The complex according to claim 3 wherein the oil is selected from the group consisting of oils of sesame, olive and almond.

8. The complex according to claim 4 wherein the oil is selected from the group consisting of oils of sesame, olive and almond.

9. The complex according to claims 1, 2, 5, 7 or 8 wherein said marrow is beef marrow.

10. The complex according to claim 3 wherein said marrow is beef marrow.

11. The complex according to claim 4 wherein said marrow is beef marrow.

12. The complex according to claim 6 wherein said marrow is beef marrow.

* * * * *